US011740370B2

(12) United States Patent
Liu et al.

(10) Patent No.: US 11,740,370 B2
(45) Date of Patent: Aug. 29, 2023

(54) RADIATION DETECTION SYSTEM AND RADIATION DETECTION METHOD FOR NEUTRON CAPTURE THERAPY SYSTEM

(71) Applicant: NEUBORON MEDTECH LTD., Jiangsu (CN)

(72) Inventors: Yuanhao Liu, Jiangsu (CN); Weilin Chen, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 9 days.

(21) Appl. No.: 17/516,775

(22) Filed: Nov. 2, 2021

(65) Prior Publication Data

US 2022/0128722 A1    Apr. 28, 2022

Related U.S. Application Data

(63) Continuation-in-part of application No. 15/913,008, filed on Mar. 6, 2018, now abandoned, which is a
(Continued)

(30) Foreign Application Priority Data

Sep. 28, 2015   (CN) .......................... 201510629532.6
Sep. 28, 2015   (CN) .......................... 201520760006.9

(51) Int. Cl.
  *G01T 3/00*   (2006.01)
  *A61N 5/10*   (2006.01)
  *H05H 3/06*   (2006.01)

(52) U.S. Cl.
  CPC .............. *G01T 3/00* (2013.01); *A61N 5/1077* (2013.01); *H05H 3/06* (2013.01); *A61N 2005/109* (2013.01); *A61N 2005/1087* (2013.01)

(58) Field of Classification Search
  CPC .. A61N 5/1071; A61N 5/1043; A61N 5/1067; A61N 2005/109; A61N 2005/1094; G01T 3/008; G01T 3/06
  See application file for complete search history.

(56) References Cited

FOREIGN PATENT DOCUMENTS

| CN | 102946944 A | 2/2013 |
| CN | 205073541 U | 3/2016 |

(Continued)

OTHER PUBLICATIONS

International Search Report of PCT/CN2016/090271, dated Sep. 26, 2016.

*Primary Examiner* — David A Vanore
(74) *Attorney, Agent, or Firm* — Locke Lord LLP; Tim Tingkang Xia, Esq.

(57) ABSTRACT

Provided is a radiation detection system for improving the accuracy of a neutron beam irradiation dose for a neutron capture therapy system. The neutron capture therapy system includes a charged particle beam, a charged particle beam inlet for passing the charged particle beam, a neutron generating unit for generating the neutron beam by means of a nuclear reaction with the charged particle beam, a beam shaping assembly for adjusting flux and quality of the neutron beam, and a beam outlet adjoining to the beam shaping assembly, the radiation detection system includes a radiation detection device arranged within the beam shaper or outside the beam shaping assembly, the radiation detection device is used for real-time detection of the overflowing neutron beam by the neutron generating unit or the generated γ-ray after the nuclear reaction of the charged particle beam with the neutron generating unit.

14 Claims, 2 Drawing Sheets

Related U.S. Application Data continuation of application No. PCT/CN2016/090271, filed on Jul. 18, 2016.

(56) References Cited

FOREIGN PATENT DOCUMENTS

| | | | |
|---|---|---|---|
| CN | 205073542 U | 3/2016 | |
| EP | 0313716 A1 | 5/1989 | |
| EP | 2805745 A1 | 11/2014 | |
| JP | 2007242422 A | * 9/2007 | |
| JP | 2008022920 A | 2/2008 | |
| TW | 201438788 A | 10/2014 | |
| WO | 2014156245 A1 | 10/2014 | |
| WO | WO-2014156245 A1 | * 10/2014 | ........... A61N 5/1048 |

* cited by examiner

RADIATION DETECTION SYSTEM AND RADIATION DETECTION METHOD FOR NEUTRON CAPTURE THERAPY SYSTEM

RELATED APPLICATION INFORMATION

This application is a continuation-in-part of and claims priority to U.S. patent application Ser. No. 15/913,008, filed Mar. 6, 2018, and titled "Radiation detection system and radiation detection method for neutron capture therapy system", which is a continuation of International Application No. PCT/CN2016/090271, filed on Jul. 18, 2016, which claims priority to Chinese Patent Application No. 201510629532.6, filed on Sep. 28, 2015 and Chinese Patent Application No. 201520760006.9, filed on Sep. 28, 2015, the disclosures of which are hereby incorporated by reference.

FIELD OF THE DISCLOSURE

The present disclosure relates generally to a radiation detection system and a radiation detection method, and, more particularly, to a radiation detection system and a radiation detection method for neutron capture therapy system.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,$\alpha$)$^7$Li neutron capture and nuclear fission reaction. As illustrated in FIGS. 1 and 2, a schematic drawing of BNCT and a nuclear reaction formula of $^{10}$B (n,$\alpha$)$^7$Li neutron capture are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

Beam detection and diagnosis which directly relates to the dose and effect of an irradiation therapy, belongs to an important subject in a neutron capture therapy system. As disclosed in the prior art, in a neutron capture therapy system, the dose of a neutron beam during irradiation is measured, for example, by attaching a gold wire for measuring a neutron beam to an irradiation object in advance, detaching the gold wire therefrom during the irradiation with a neutron beam, and measuring an amount of activated gold of the gold wire. It is intended to control (for example, stop) the neutron capture therapy system so as to irradiate the irradiation object with the neutron beam with a desired dose on the basis of the measured dose.

However, in this case, for example, when a dose rate of a neutron beam varies for some reasons after measuring the amount of activated gold of the gold wire, it may not be possible to cope with this variation and it may thus be difficult to irradiate an irradiation object with a neutron beam with a desired dose. That is to say, in the aforementioned neutron capture therapy system, the irradiation dose of the radiation cannot be detected in real time.

Accordingly, it is necessary to provide a radiation detection system and a radiation detection method for neutron capture therapy system capable of improving the accuracy of a neutron beam irradiation dose.

The statements in this section merely provide background information related to the present disclosure and may not constitute prior art.

SUMMARY

One aspect of the present disclosure is to improve radiation detection system for neutron capture therapy system capable of improving the accuracy of a neutron beam irradiation dose. Wherein the neutron capture therapy system includes a charged particle beam, a beam expanding device expander configured to expand the charged particle beam, a charged particle beam inlet for passing the charged particle beam expanded by the beam expander, a neutron generating unit generating a neutron beam by means of a nuclear reaction with the charged particle beam, and a beam shaping assembly for adjusting flux and quality of the neutron beam generated by the neutron generating unit and a beam outlet adjoining to the beam shaping assembly, wherein the neutron beam generating unit is arranged into the beam shaping assembly, and the radiation detection system includes a radiation detection device arranged downstream of the beam expanding device expander and upstream of the neutron beam generating unit, the radiation detection device is used to detect the neutron beam overflowing from or $\gamma$ ray generated by the neutron generating unit in real time after the charged particle beam and the neutron generating unit are subjected to the nuclear reaction.

Implementations of this aspect may include one or more of the following features.

Preferably, the radiation detection system further includes a control device, and wherein the control device sends a human-perceivable signal according to a detection result of the radiation detection system so as to confirm subsequent operation of the neutron capture therapy system. The human-perceivable signal may be a signal which can be perceived by human functional organs such as auditory sense, visual sense, tactile sense or smell sense. For example, the signal is one or more forms in various signals such as a sound-making alarm, an alarm lamp, a vibrating signal and a pungent smell emitting signal.

The neutron capture therapy system further includes an accelerator for accelerating the charged particle beam, and the control device includes a display unit for displaying the detection result of the radiation detection system and a control unit for feeding the detection result back to the accelerator so as to confirm subsequent operation of the accelerator, and the display unit may be common display equipment such as a television or a liquid crystal display.

More particularly, the radiation detection device is an ionization chamber or a scintillator, the radiation detection system calculates the intensity of the neutron beam according to detection signal, so that the charged particle beam is adjusted and the irradiation dose is controlled.

A common radiation detection device for real-time detection may have two different detection principles, namely an ionization chamber and a scintillator detector, can be realized. Those adopting ionization chamber structures as substrates include an He-3 proportional counter, a $BF_3$ proportional counter, a fission chamber and a boron ionization chamber. The scintillator detector may be divided into organic and inorganic materials, and for the purpose of detecting thermal neutrons, the scintillator detector mainly adds high thermal neutron capture section elements such as Li or B. In short, most of neutron energies detected by this type of detectors are the thermal neutrons, which are all heavy charged particles and nuclear fission fragments released by means of a capture or nuclear fission reaction between elements and neutrons, a great number of ion pairs are generated in the ionization chamber or the scintillator detector, and after the charges are collected, a current signal may be converted into a voltage pulse signal via appropriate circuit conversion. A neutron signal and a γ signal can be easily distinguished from each other by analyzing the magnitude of a voltage pulse. In a high-intensity neutron field such as a BNCT, the gas pressure of the ionization chamber, the concentration of coating of fissionable materials or boron or the concentration of the high neutron capture section elements in the scintillator detector can be appropriately reduced, so the sensitivity to neutrons can be effectively reduced, and the situation of signal saturation is avoided.

More preferably, the neutron beam detection system of present embodiment is a scintillator detector, and after certain materials absorb energy, visible light will be emitted, and the materials are referred to as scintillating materials. It utilizes ionizing radiation to excite an electron in a crystal or molecule to an exciting state, fluorescent light emitted when the electron returns to a base state is used for monitoring a neutron beam after being collected. The visible light emitted after the scintillator detector interacts with the neutron beam can be converted into an electron by utilizing a photomultiplier, and the electron is multiplied and amplified, wherein the multiplication and amplification rate of the electron can reach $10^7$ to $10^8$ usually. The quantity of electrons output from an anode is in direct proportion to energy of an incident neutron beam, and therefore the scintillator detector can measure the energy of the neutron beam.

The beam shaping assembly may include a reflector, a moderator surrounded by the reflector and adjoining to the neutron generating unit, a thermal neutron absorber adjoining to the moderator and a radiation shield arranged into the beam shaping assembly.

In another aspect of the present disclosure is to improve radiation detection method for neutron capture therapy system capable of improving the accuracy of a neutron beam irradiation dose. Wherein the neutron capture therapy system includes a charged particle beam, a charged particle beam inlet for passing the charged particle beam, a neutron generating unit generating a neutron beam by means of a nuclear reaction with the charged particle beam, and a beam shaping assembly for adjusting flux and quality of the neutron beam generated by the neutron generating unit and a beam outlet adjoining to the beam shaping assembly, wherein the neutron beam generating unit is arranged into the beam shaping assembly, and the radiation detection system includes a radiation detection device arranged inside or outside the beam shaping assembly, the radiation detection device is used to detect the neutron beam overflowing from or γ ray generated by the neutron generating unit after the charged particle beam and the neutron generating unit are subjected to the nuclear reaction, and wherein the radiation detection method includes a detection step for detecting the neutron beam overflowing from or γ ray generated by the neutron generating unit in real time after the charged particle beam and the neutron generating unit are subjected to the nuclear reaction.

Implementations of this aspect may include one or more of the following features.

The radiation detection method further includes a controlling step for controlling subsequent operation of the neutron capture therapy system according to a detection result obtained in the detection step.

More particularly, the neutron capture therapy system further includes an accelerator for accelerating the charged particle beam, and the controlling step for controlling subsequent operation of the accelerator according to the detection result obtained in the detection step.

The radiation detection device further includes a display unit, the detection method includes a display step for displaying the detection result obtained in the detection step.

The detection method further includes a calculation step for calculating the intensity of the neutron beam according to detection signal, so that the charged particle beam is adjusted and the irradiation dose is controlled.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

FIG. 4B is a cross-sectional schematic view of the radiation field of the proton beam when the beam expander 20 is turned on.

Figure 1:
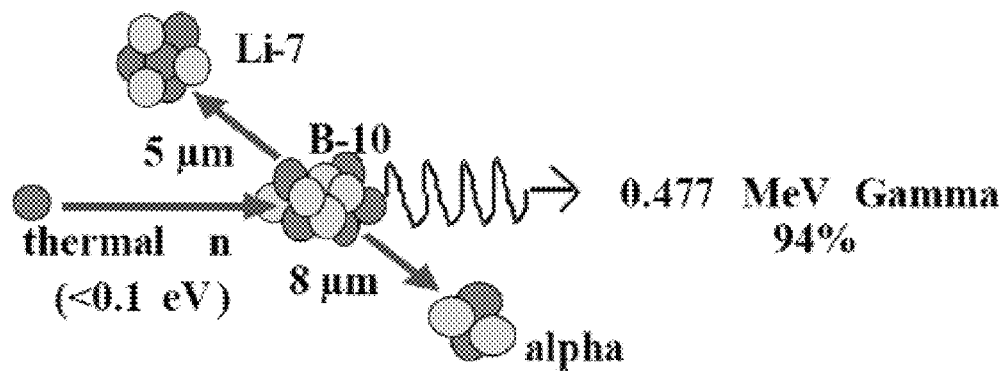
FIG. 1 is a schematic view of boron neutron capture reaction.
Figure 2:
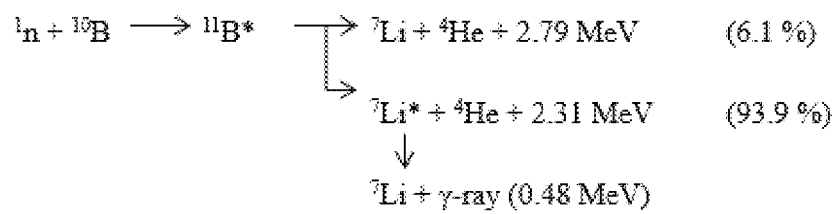
FIG. 2 is a nuclear reaction formula of $^{10}B$ $(n,\alpha)^7Li$ neutron capture.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components comprise, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7$Li (p, n)$^7$Be and $^9$Be (p, n)$^9$B and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n) $^7$Be asks for more than $^9$Be (p, n)$^9$B does because of low melting point and poor thermal conductivity coefficient of the metal (lithium) target. In these embodiments of the present disclosure is $^7$Li (p, n) $^7$Be.

No matter BNCT neutron sources are from the nuclear reactor or the nuclear reactions between the accelerator charged particles and the target, only mixed radiation fields are produced, that is, beams comprise neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>$1\times10^9$ n/cm$^2$s
Fast neutron contamination <$2\times10^{-13}$ Gy-cm$^2$/n
Photon contamination <$2\times10^{-13}$ Gy-cm$^2$/n
Thermal to epithermal neutron flux ratio <0.05
Epithermal neutron current to flux ratio >0.7

Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons are considered as contamination. The dose exhibit positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than $2*10^{-13}$Gy-cm$^2$/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is called as advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time <=30 min (proton current for accelerator is 10 mA)
2. 30.0RBE-Gy treatable depth >=7 cm
3. The maximum tumor dose>=60.0RBE-Gy
4. The maximum dose of normal brain tissue<=12.5RBE-Gy
5. The maximum skin dose<=11.0RBE-Gy Note: RBE stands for relative biological effectiveness. Since photons and neutrons express different biological effectiveness, the dose above should be multiplied with RBE of different tissues to obtain equivalent dose.

Figure 3:
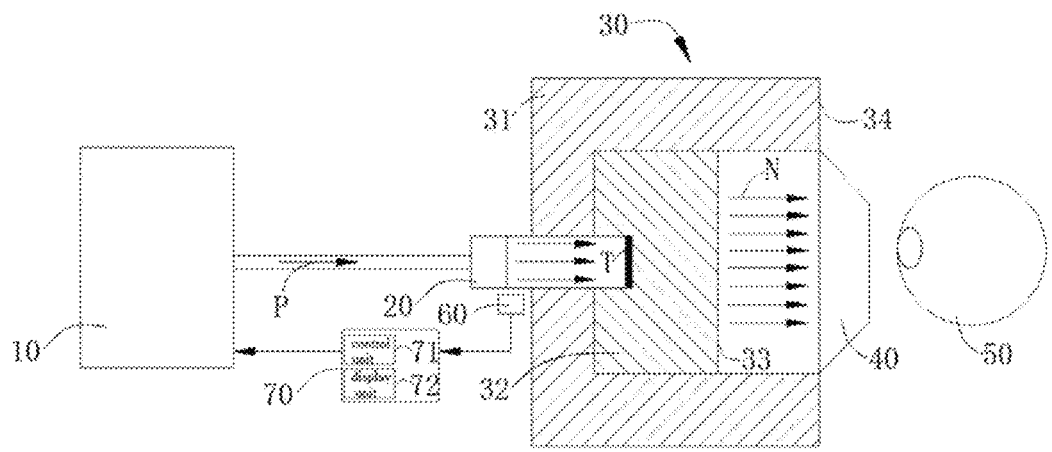
FIG. 3 is a schematic view of the radiation detection system for neutron capture therapy system in one embodiment of the present disclosure.
Figure 4A:
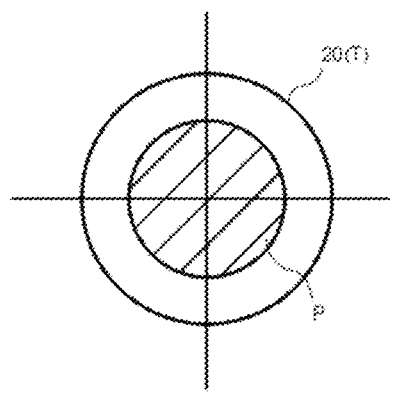
FIG. 4A is a cross-sectional schematic view of the radiation field of the proton beam when the beam expander 20 is turned off.
Figure 4B:
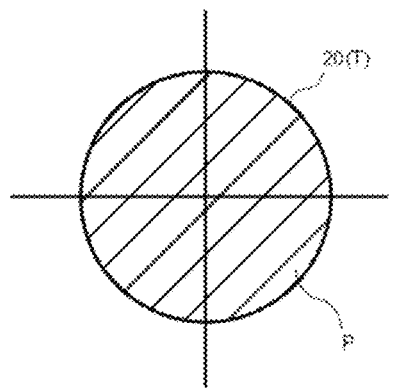
Figure 5A:
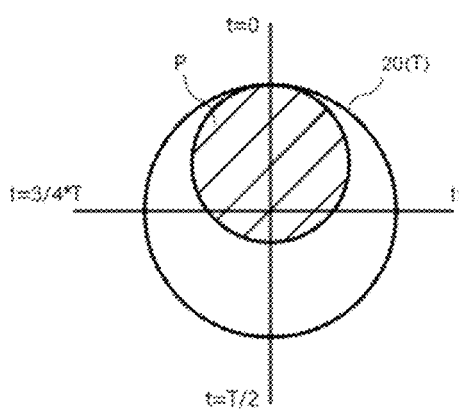
FIG. 5A is a cross-sectional schematic view of the radiation field of the proton beam when time t=0 in a time period T.
Figure 5B:
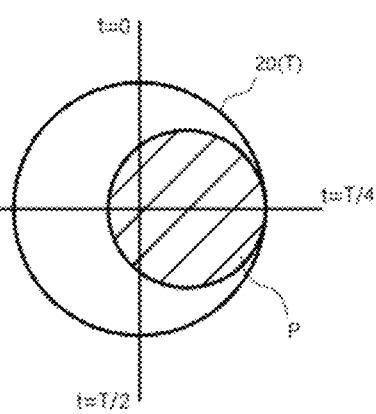
FIG. 5B is a cross-sectional schematic view of the radiation field of the proton beam when time t=T/4 in a time period T.
Figure 5C:
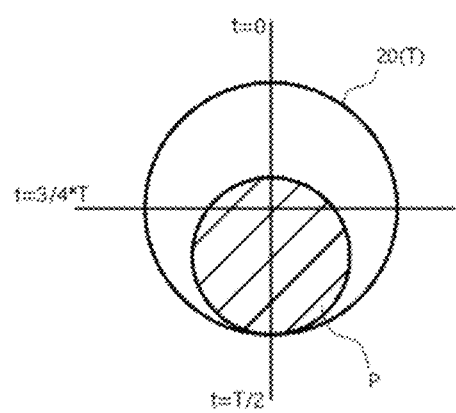
FIG. 5C is a cross-sectional schematic view of the radiation field of the proton beam when time t=T/2 in a time period T.
Figure 5D:
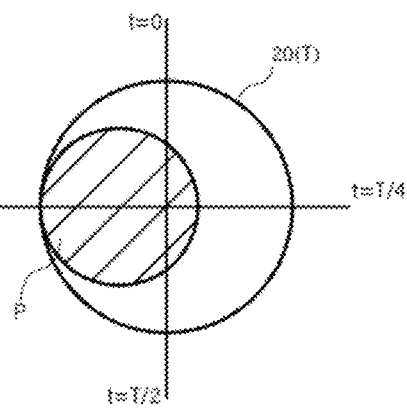
FIG. 5D is a cross-sectional schematic view of the radiation field of the proton beam when time t=3/4*T in a time period T.

Referring to FIG. 3, one aspect of the embodiment aims at providing a radiation detection system used for improving the accuracy of the irradiation dosage of the neutron beam of a neutron capture therapy system. Another aspect of the embodiment provides a radiation detection method used for improving the accuracy of the irradiation dosage of the neutron beam of the neutron capture therapy system.

The neutron capture therapy system includes an accelerator 10, a beam expander 20, a charged particle beam inlet for passing a charged particle beam P, the charged particle beam P, a neutron beam generating unit T generating a neutron beam N by means of a nuclear reaction with the charged particle beam P, a beam shaping assembly 30 for adjusting flux and quality of the neutron beam generated by the neutron beam generating unit T, a beam outlet 40 adjoining to the beam shaping assembly 30, a irradiated body 50 irradiated by a beam emitted out from the beam outlet 40.

The accelerator 10 is used for accelerating the charged particle beam P, and may be an accelerator suitable for an accelerator-type neutron capture therapy system such as a cyclotron or a linear accelerator. The charged particle beam P is preferably a proton beam. The beam expander 20 is disposed between the accelerator 10 and the neutron beam generating unit T. The charged particle beam inlet abuts the neutron beam generating unit T and is accommodated in the beam shaping assembly 30. Three arrows between the neutron beam generating unit T and the beam expander as shown in FIG. 3 serve as the charged particle beam inlet. The neutron beam generating unit T is accommodated in the beam shaping assembly 30. The neutron beam generating unit T is preferably lithium metal. The beam shaping assembly 30 includes a reflector 31, a moderator 32 which is surrounded by the reflector 31 and abuts the neutron beam generating unit T, a thermal neutron absorber 33 abutting the moderator 32, and a radiation shield 34 disposed in the beam shaping assembly 30. The neutron beam generating unit T and the charged particle beam P emitted from the charged particle beam inlet perform a nuclear reaction to generate the neutron beam N. The neutron beam defines a principal axis, the moderator 32 moderates neutrons generated by the neutron beam generating unit T to an epithermal neutron energy region, the reflector 31 guides the neutrons deviating from the principal axis back to the principal axis so as to improve the intensity of an epithermal neutron beam, the thermal neutron absorber 33 is used for absorbing thermal neutrons so as to avoid excess doses caused with normal tissues of a superficial layer during therapy, and the radiation shield 34 is used for shielding leaked neutrons and photons so as to reduce a normal tissue dose of a non-irradiation region. The beam outlet 40 may also be referred to as a neutron beam convergence part or a collimator, which reduces the widths of neutron beams so as to gather the neutron beams. The neutron beams emitted from the beam outlet 40 irradiate a target part of the irradiated body 50.

The beam expander 20 produces a desired radiation field when a controlled extraction of the proton beam from an accelerator is coupled with strictly prescribed patterns of the motion of the beam spot. The beam expander 20 moves a beam spot in a predetermined way to produce a desired dose distribution. The beam expander 20 is arranged with compound coils, a rotating set of permanent magnets, or electrostatic deflectors to accomplish similar functions. The beam expander 20 has a distinct advantage over the scattering systems in minimizing the material in the beam path, maintaining the beam range, reducing fragmentation of the beam particles, and decreasing the background radiation for the patients.

Referring to FIGS. 4A-4B and FIGS. 5A-5D, the radiation field of the proton beam P generated by turning on the beam expander is significantly larger than the radiation field of the proton beam P generated by turning off the beam expander. Taking a clockwise time period T, such as 1s, for example, when time t=0, the radiation field of the proton beam is on the uppermost area of the target material T; when time t=T/4, the radiation field of the proton beam is on the rightmost area of the target material T; when time t=T/2, the radiation field of the proton beam is on the lowermost area of the target material T; when time t=3/4*T, the radiation field of the proton beam is on the leftmost area of the target material T. Therefore, within a time period T, the proton beam can irradiate the entire target T, thereby expanding the radiation field of the proton beam P.

An example of the beam expander 20 is a compact, cost-effective scanning magnets with separate transverse and longitudinal laminated deflection magnets. It provides a combination of deflection angle and low inductances which allow for fast spot placement over a large scan field. The scanning magnet system allows the proton beam to reach any point in the scan field at the isocenter plane at the highest specified beam energy. It moves quickly between spot positions, and occupies as little space as possible in the beam path. The matching scan amplifier system provides the current to maintain the beam spot precisely in position, then drive the magnet load to the next spot position at high slew rate with minimal settle time.

The radiation detection system used for improving the accuracy of the irradiation dosage of the neutron beam of the neutron capture therapy system includes a radiation detection device 60 arranged inside or outside the beam shaping assembly 30, and a control device 70. The radiation detection device 60 is used for detecting the neutron beam overflowing from or γ-ray generated by the neutron generating unit T in real time after the charged particle beam P and the neutron generating unit T are subjected to a nuclear reaction.

The control device 70 sends a human-perceivable signal according to a detection result of the radiation detection system so as to confirm subsequent operation of the neutron capture therapy system. The human-perceivable signal may be a signal which can be perceived by human functional organs such as auditory sense, visual sense, tactile sense or smell sense. For example, the signal is one or more forms in various signals such as a sound-making alarm, an alarm lamp, a vibrating signal and a pungent smell emitting signal.

The neutron capture therapy system further includes an accelerator for accelerating the charged particle beam, and the control device 70 includes a display unit 72 for displaying the detection result of the radiation detection system and a control unit 71 for feeding the detection result back to the accelerator so as to confirm subsequent operation of the accelerator, and the display unit may be common display equipment such as a television or a liquid crystal display.

A common radiation detection device for real-time detection may have two different detection principles, namely an ionization chamber and a scintillator detector, can be realized. Those adopting ionization chamber structures as substrates include an He-3 proportional counter, a $BF_3$ proportional counter, a fission chamber and a boron ionization chamber. The scintillator detector may be divided into organic and inorganic materials, and for the purpose of detecting thermal neutrons, the scintillator detector mainly adds high thermal neutron capture section elements such as Li or B. In short, most of neutron energies detected by this type of detectors are the thermal neutrons, which are all heavy charged particles and nuclear fission fragments released by means of a capture or nuclear fission reaction between elements and neutrons, a great number of ion pairs are generated in the ionization chamber or the scintillator detector, and after the charges are collected, a current signal may be converted into a voltage pulse signal via appropriate circuit conversion. A neutron signal and a γ signal can be easily distinguished from each other by analyzing the magnitude of a voltage pulse. In a high-intensity neutron field such as a BNCT, the gas pressure of the ionization chamber, the concentration of coating of fissionable materials or boron or the concentration of the high neutron capture section elements in the scintillator detector can be appropriately reduced, so the sensitivity to neutrons can be effectively reduced, and the situation of signal saturation is avoided.

More particularly, the neutron beam detection system in the embodiment adopts the ionization chamber. When passing through the ionization chamber, a neutron beam ionizes gas molecules inside the fission chamber or a wall portion of the ionization chamber to generate an electron and an ion with a positive charge, the electron and the positive charge ion are referred to as the aforementioned ion pair. The interior of the ionization chamber has an external electric field high voltage, so the electron moves toward a central anode wire, and the positive charge ion moves toward a surrounding cathode wall, thus generating an electronic pulse signal which can be measured. An energy needed for generating an ion pair by gas molecules is referred to as an average ionizing energy, the value varying with a gas type. For example, the average ionizing energy of air is about 34 eV. If a neutron beam of 340 keV exists, the air will generate about 10 k ion pairs.

More preferably, the neutron beam detection system of another embodiment is a scintillator detector, and after certain materials absorb energy, visible light will be emitted, and the materials are referred to as scintillating materials. It utilizes ionizing radiation to excite an electron in a crystal or molecule to an exciting state, fluorescent light emitted when the electron returns to a base state is used for monitoring a neutron beam after being collected. The visible light emitted after the scintillator detector interacts with the neutron beam can be converted into an electron by utilizing a photomultiplier, and the electron is multiplied and amplified, wherein the multiplication and amplification rate of the electron can reach $10^7$ to $10^8$ usually. The quantity of electrons output from an anode is in direct proportion to energy of an incident neutron beam, and therefore the scintillator detector can measure the energy of the neutron beam or γ-ray.

The radiation detection system calculates the intensity of the neutron beam according to detection signal, so that the charged particle beam is adjusted and the irradiation dose is controlled.

As is well known by those skilled in the art that regardless of arrangement of the neutron beam detection system inside or adjacent to the beam shaping assembly, a detection device capable of detecting intensity variation and spatial distribution of the neutron beam in the beam shaping assembly can be adopted.

In another aspect of the present disclosure is to improve radiation detection method for neutron capture therapy system capable of improving the accuracy of a neutron beam irradiation dose. Wherein the neutron capture therapy system includes a charged particle beam, a charged particle beam inlet for passing the charged particle beam, a neutron generating unit generating a neutron beam by means of a nuclear reaction with the charged particle beam, and a beam shaping assembly for adjusting flux and quality of the neutron beam generated by the neutron generating unit and a beam outlet adjoining to the beam shaping assembly, wherein the neutron beam generating unit is arranged into the beam shaping assembly, and the radiation detection system includes a radiation detection device arranged inside or outside the beam shaping assembly, the radiation detection device is used to detect the neutron beam overflowing from or γ ray generated by the neutron generating unit after the charged particle beam and the neutron generating unit are subjected to the nuclear reaction, and wherein the radiation detection method includes a detection step for detecting the neutron beam overflowing from or γ ray generated by the neutron generating unit in real time after the charged particle beam and the neutron generating unit are subjected to the nuclear reaction.

The radiation detection method further includes a controlling step for controlling subsequent operation of the neutron capture therapy system according to a detection result obtained in the detection step.

More particularly, the neutron capture therapy system further includes an accelerator for accelerating the charged particle beam, and the controlling step for controlling subsequent operation of the accelerator according to the detection result obtained in the detection step.

The radiation detection device further includes a display unit, the detection method includes a display step for displaying the detection result obtained in the detection step.

The detection method further includes a calculation step for calculating the intensity of the neutron beam according to detection signal, so that the charged particle beam is adjusted and the irradiation dose is controlled.

The radiation detection system for the neutron capture therapy system disclosed by the present disclosure is not limited to the contents in the foregoing embodiments and the structures shown in the drawings. All obvious changes, replacements or modifications made on materials, shapes and positions of members on the basis of the present disclosure fall within the scope of protection of the present disclosure.

What is claimed is:

1. A radiation detection system for a neutron capture therapy system, wherein the neutron capture therapy system comprises:
   a charged particle beam;
   a beam expander configured to expand the charged particle beam;
   a charged particle beam inlet configured for passing the charged particle beam expanded by the beam expander;
   a neutron beam generating unit configured for generating a neutron beam by means of a nuclear reaction with the charged particle beam;
   a beam shaping assembly configured for adjusting flux and quality of the neutron beam generated by the neutron beam generating unit; and
   a beam outlet adjoining to the beam shaping assembly,
   wherein the neutron beam generating unit is arranged into the beam shaping assembly, and the radiation detection system comprises a radiation detection device arranged downstream of the beam expander and upstream of the neutron beam generating unit, and the radiation detection device is configured to detect the neutron beam overflowing from the neutron beam generating unit in real time after the charged particle beam and the neutron beam generating unit are subjected to the nuclear reaction.

2. The radiation detection system according to claim 1, wherein the radiation detection system further comprises a control device, and wherein the control device sends a human-perceivable signal according to a detection result of the radiation detection system so as to confirm subsequent operation of the neutron capture therapy system.

3. The radiation detection system according to claim 2, wherein the neutron capture therapy system further comprises an accelerator configured for accelerating the charged particle beam, and the control device comprises a display unit configured for displaying the detection result of the radiation detection system and a control unit configured for feeding the detection result back to the accelerator so as to confirm subsequent operation of the accelerator.

4. The radiation detection system according to claim 3, wherein the beam expander is disposed between the accelerator and the neutron beam generating unit.

5. The radiation detection system according to claim 1, wherein the radiation detection device is an ionization chamber or a scintillator, and the radiation detection system is configured to calculate an intensity of the neutron beam according to a detection signal, and to adjust the charged particle beam and to control an irradiation dose of the neutron beam based on the intensity of the neutron beam.

6. The radiation detection system according to claim 1, wherein the beam shaping assembly comprises a reflector, a moderator surrounded by the reflector and adjoining to the neutron beam generating unit, a thermal neutron absorber adjoining to the moderator and a radiation shield arranged into the beam shaping assembly.

7. The radiation detection system according to claim 1, wherein the charged particle beam inlet is located between the beam expander and the neutron beam generating unit.

8. A radiation detection method for a neutron capture therapy system, wherein the neutron capture therapy system comprises:
   a charged particle beam;
   a beam expander configured to expand the charged particle beam;
   a charged particle beam inlet configured for passing the charged particle beam expanded by the beam expander;
   a neutron beam generating unit configured for generating a neutron beam by means of a nuclear reaction with the charged particle beam;
   a beam shaping assembly configured for adjusting flux and quality of the neutron beam generated by the neutron beam generating unit; and
   a beam outlet adjoining to the beam shaping assembly,
   wherein the neutron beam generating unit is arranged into the beam shaping assembly, and a radiation detection system configured to perform the radiation detection method comprises a radiation detection device arranged downstream of the beam expander and upstream of the neutron beam generating unit, the radiation detection device is configured to detect the neutron beam overflowing from the neutron beam generating unit after the charged particle beam and the neutron beam generating unit are subjected to the nuclear reaction, and
   wherein the radiation detection method comprises a detection step for detecting the neutron beam overflowing from the neutron beam generating unit in real time after the charged particle beam and the neutron beam generating unit are subjected to the nuclear reaction.

9. The radiation detection method according to claim 8, wherein the radiation detection method further comprises a controlling step for controlling subsequent operation of the neutron capture therapy system according to a detection result obtained in the detection step.

10. The radiation detection method according to claim 9, wherein the neutron capture therapy system further comprises an accelerator for accelerating the charged particle beam, and the controlling step for controlling subsequent operation of the accelerator according to the detection result obtained in the detection step.

11. The radiation detection method according to claim 10, wherein the radiation detection device comprises a display unit, the radiation detection method comprises a display step for displaying the detection result obtained in the detection step.

12. The radiation detection method according to claim 10, wherein the radiation detection method comprises a calculation step for calculating an intensity of the neutron beam according to a detection signal, so that the charged particle beam is adjusted and an irradiation dose of the neutron beam is controlled based on the intensity of the neutron beam.

13. The radiation detection method according to claim 10, wherein the beam expander is disposed between the accelerator and the neutron beam generating unit.

14. The radiation detection method according to claim 8, wherein the charged particle beam inlet is located between the beam expander and the neutron beam generating unit.

* * * * *